US012016642B2

(12) United States Patent
Schoen et al.

(10) Patent No.: US 12,016,642 B2
(45) Date of Patent: Jun. 25, 2024

(54) CONSTELLATIONS FOR TRACKING INSTRUMENTS, SUCH AS SURGICAL INSTRUMENTS, AND ASSOCIATED SYSTEMS AND METHODS

(71) Applicant: Proprio, Inc., Seattle, WA (US)

(72) Inventors: Jason A. Schoen, Seattle, WA (US); Stephen A. Morse, Woodinville, WA (US); Nicholas Hirdt, Seattle, WA (US)

(73) Assignee: PROPRIO, INC., Seattle, WA (US)

( * ) Notice: Subject to any disclaimer, the term of this patent is extended or adjusted under 35 U.S.C. 154(b) by 0 days.

(21) Appl. No.: 17/469,599

(22) Filed: Sep. 8, 2021

(65) Prior Publication Data

US 2023/0073934 A1 Mar. 9, 2023

(51) Int. Cl.
*A61B 34/20* (2016.01)
*A61B 90/00* (2016.01)

(52) U.S. Cl.
CPC .............. *A61B 34/20* (2016.02); *A61B 90/39* (2016.02); *A61B 2034/2055* (2016.02); *A61B 2090/3983* (2016.02)

(58) Field of Classification Search
CPC . A61B 34/20; A61B 90/39; A61B 2034/2055; A61B 2090/3983
See application file for complete search history.

(56) References Cited

U.S. PATENT DOCUMENTS

| | | | |
|---|---|---|---|
| 3,965,572 | A | 6/1976 | Strybel |
| 6,675,040 | B1 | 1/2004 | Cosman |
| 6,985,765 | B2 | 1/2006 | Morita et al. |
| 8,295,909 | B2 | 10/2012 | Goldbach |
| 8,384,912 | B2 | 2/2013 | Charny et al. |
| 8,657,809 | B2 | 2/2014 | Schoepp |

(Continued)

FOREIGN PATENT DOCUMENTS

| | | |
|---|---|---|
| EP | 1504713 B1 | 7/2008 |
| EP | 2139419 A1 | 1/2010 |

(Continued)

OTHER PUBLICATIONS

International Search Report and Written Opinion received in Application No. PCT/US22/13490, dated May 6, 2022, 9 pages.

(Continued)

*Primary Examiner* — Joel Lamprecht
*Assistant Examiner* — Nyrobi Celestine
(74) *Attorney, Agent, or Firm* — Perkins Coie LLP

(57) ABSTRACT

Tracking constellations for use with surgical instruments, and associated systems and methods, are disclosed herein. In some embodiments, a tracking constellation includes (i) a support, (ii) a plurality of first standoffs extending from the support to a first height, and (iii) a plurality of second standoffs extending from the support to a second height different than the first height. The tracking constellation can further include a plurality of markers mounted to corresponding ones of the first standoffs or the second standoffs. The markers can lay in a common plane. The support can extend at a generally orthogonal angle to an instrument when the tracking constellation is coupled to the instrument such that the common plane is angled relative to the instrument.

17 Claims, 10 Drawing Sheets

(56) References Cited

U.S. PATENT DOCUMENTS

| | | |
|---|---|---|
| 8,885,177 B2 | 11/2014 | Ben-yishai et al. |
| D720,851 S | 1/2015 | Yang et al. |
| 8,933,935 B2 | 1/2015 | Yang et al. |
| D727,497 S | 4/2015 | Yang et al. |
| D768,296 S | 10/2016 | Corrao, Jr. et al. |
| D778,441 S | 2/2017 | Corrao, Jr. et al. |
| 9,916,691 B2 | 3/2018 | Takano et al. |
| 10,013,777 B2 | 7/2018 | Mariampillai et al. |
| 10,034,713 B2 | 7/2018 | Yang et al. |
| 10,074,177 B2 | 9/2018 | Piron et al. |
| 10,143,523 B2 | 12/2018 | Mariampillai et al. |
| 10,165,981 B2 | 1/2019 | Schoepp |
| 10,194,131 B2 | 1/2019 | Casas |
| 10,398,514 B2 | 9/2019 | Ryan et al. |
| 10,426,554 B2 | 10/2019 | Siewerdsen et al. |
| 10,433,916 B2 | 10/2019 | Schneider et al. |
| 10,463,434 B2 | 11/2019 | Siegler et al. |
| 10,575,906 B2 | 3/2020 | Wu |
| 10,650,573 B2 | 5/2020 | Youngquist et al. |
| 10,653,495 B2 | 5/2020 | Gregerson et al. |
| 10,667,868 B2 | 6/2020 | Malackowski |
| 10,806,539 B1 | 10/2020 | Richter et al. |
| 10,810,799 B2 | 10/2020 | Tepper et al. |
| 10,828,114 B2 | 11/2020 | Abhari et al. |
| 10,949,986 B1 | 3/2021 | Colmenares et al. |
| 2003/0093904 A1 | 5/2003 | Makkonen |
| 2003/0210812 A1 | 11/2003 | Khamene et al. |
| 2003/0225329 A1 | 12/2003 | Rossner et al. |
| 2004/0169673 A1 | 9/2004 | Crampe et al. |
| 2005/0070789 A1 | 3/2005 | Aferzon |
| 2005/0096536 A1 | 5/2005 | Peterson |
| 2007/0239169 A1* | 10/2007 | Plaskos ............ A61B 90/39 606/96 |
| 2008/0051768 A1* | 2/2008 | Stumpf ............ A61B 90/39 606/1 |
| 2010/0099981 A1 | 4/2010 | Fishel |
| 2011/0263971 A1* | 10/2011 | Nikou ............ A61B 90/39 600/424 |
| 2014/0288578 A1* | 9/2014 | Solar ............ A61B 17/00234 606/130 |
| 2016/0256225 A1* | 9/2016 | Crawford ............ A61B 34/30 |
| 2016/0354582 A1 | 12/2016 | Yu et al. |
| 2017/0000583 A1* | 1/2017 | Lechner ............ A61B 34/20 606/130 |
| 2017/0202626 A1 | 7/2017 | Kula et al. |
| 2018/0064496 A1* | 3/2018 | Hladio ............ A61B 90/361 |
| 2018/0078316 A1 | 3/2018 | Schaewe et al. |
| 2019/0038362 A1 | 2/2019 | Nash et al. |
| 2019/0129177 A1 | 5/2019 | Roimi et al. |
| 2019/0183584 A1 | 6/2019 | Schneider et al. |
| 2019/0209080 A1 | 7/2019 | Gullotti et al. |
| 2019/0289284 A1 | 9/2019 | Smith et al. |
| 2019/0290366 A1 | 9/2019 | Pettersson et al. |
| 2019/0336222 A1 | 11/2019 | Schneider et al. |
| 2020/0105065 A1 | 4/2020 | Youngquist et al. |
| 2020/0170718 A1 | 6/2020 | Peine |
| 2020/0242755 A1 | 7/2020 | Schneider et al. |
| 2020/0297427 A1 | 9/2020 | Cameron et al. |
| 2021/0038340 A1 | 2/2021 | Itkowitz et al. |
| 2021/0045618 A1 | 2/2021 | Stricko et al. |
| 2021/0045813 A1 | 2/2021 | Wickham et al. |
| 2021/0093394 A1* | 4/2021 | Yang ............ A61B 17/1757 |
| 2021/0106342 A1 | 4/2021 | Blackwell |
| 2021/0113241 A1 | 4/2021 | Forster et al. |
| 2021/0153953 A1 | 5/2021 | Mariampillai et al. |
| 2021/0192763 A1 | 6/2021 | Liu et al. |
| 2021/0196385 A1 | 7/2021 | Shelton et al. |
| 2022/0125520 A1* | 4/2022 | Crawford ............ A61B 17/0206 |

FOREIGN PATENT DOCUMENTS

| | | | |
|---|---|---|---|
| EP | 1924197 B1 | 10/2017 | |
| EP | 3197382 A4 | 6/2018 | |
| EP | 3102141 B1 | 8/2019 | |
| EP | 3076892 B1 | 10/2019 | |
| EP | 3046500 B1 * | 8/2020 | ....... A61B 17/00234 |
| WO | 2007115825 A1 | 10/2007 | |
| WO | 2008130354 A1 | 10/2008 | |
| WO | 2010067267 A1 | 6/2010 | |
| WO | 2017042171 A1 | 3/2017 | |
| WO | 2020163316 A1 | 8/2020 | |
| WO | 2021003401 A1 | 1/2021 | |

OTHER PUBLICATIONS

U.S. Appl. No. 17/140,885, titled "Methods and Systems for Registering Preoperative Image Data To Intraoperative Image Data of a Scene, Such as a Surgical Scene," and filed Jan. 4, 2021.

\* cited by examiner

CONSTELLATIONS FOR TRACKING INSTRUMENTS, SUCH AS SURGICAL INSTRUMENTS, AND ASSOCIATED SYSTEMS AND METHODS

TECHNICAL FIELD

The present technology generally relates to methods, systems, and devices for tracking instruments, and more particularly to tracking constellations for attachment to surgical tools.

BACKGROUND

In a mediated reality system, an image processing system adds, subtracts, and/or modifies visual information representing an environment. For surgical applications, a mediated reality system may enable a surgeon to view a surgical site from a desired perspective together with contextual information that assists the surgeon in more efficiently and precisely performing surgical tasks. Such contextual information may include the position of objects within the scene, such as surgical instruments. Specifically, the mediated reality system can include trackers configured to track markers or other identifiers fixed to objects of interest within the scene. While the objects of interest can be tracked when the markers are within view of the trackers, it can be difficult to track the objects when the markers are out of view of the trackers. Likewise, tracking accuracy can be diminished if the markers move relative to the object after calibration.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Figure 1:
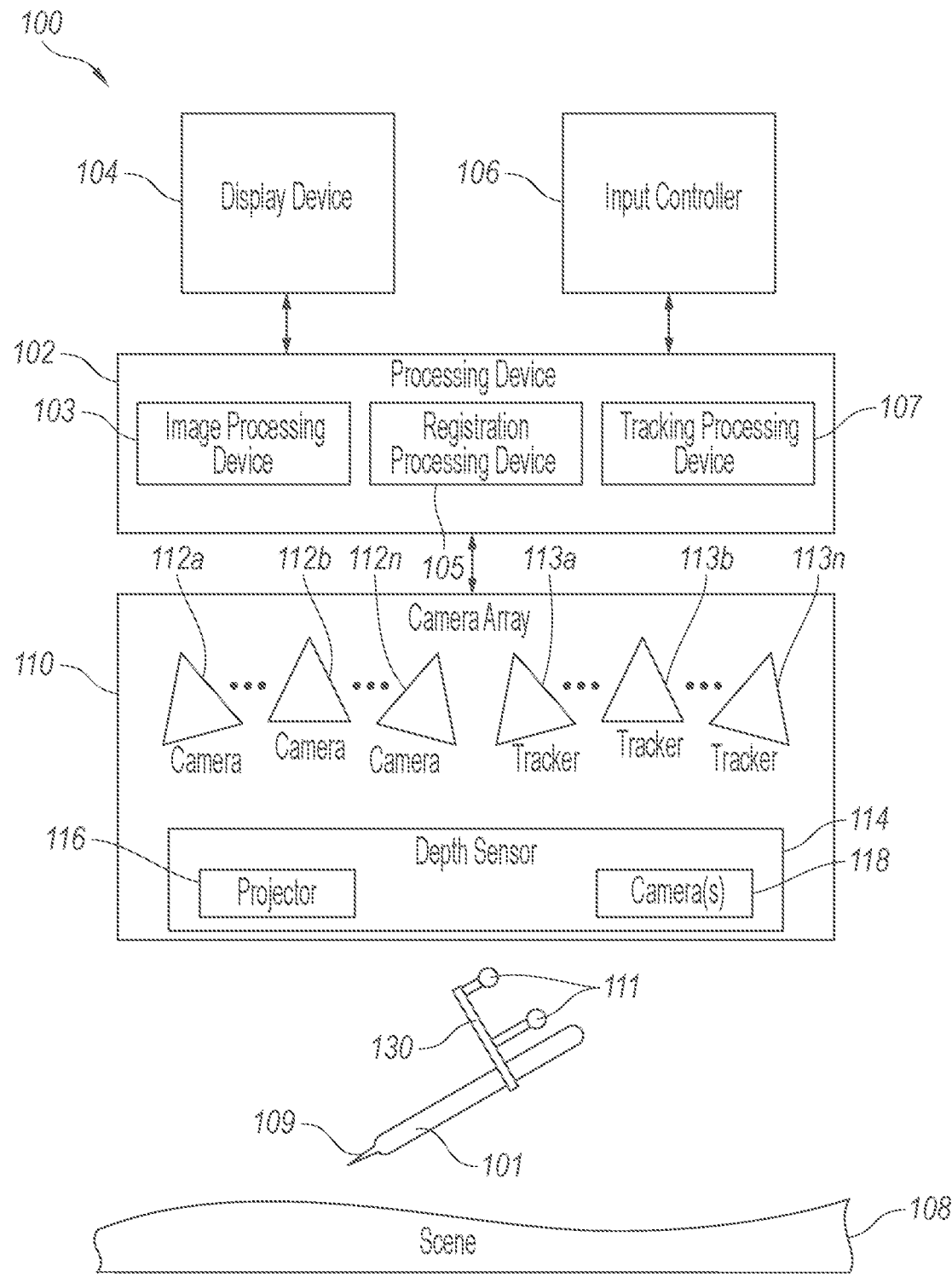
FIG. 1 is a schematic view of an imaging system in accordance with embodiments of the present technology.

Aspects of the present technology are directed generally to tracking constellations for use with instruments, such as surgical instruments, and associated system and methods. In several of the embodiments described below, for example, a tracking constellation includes (i) a support, (ii) a plurality of first standoffs extending from the support to a first height, and (iii) a plurality of second standoffs extending from the support to a second height different than the first height. The tracking constellation can further include a plurality of markers mounted to corresponding ones of the first standoffs and the second standoffs. In some embodiments, the markers lay in a common plane. The tracking constellation can be rigidly coupled to an instrument, such as a surgical instrument. When the tracking constellation is coupled to the instrument, the support can extend at a generally orthogonal angle to a longitudinal axis of the instrument such that the common plane is angled relative to the instrument.

In some aspects of the present technology, mounting the markers at an angle relative to the instrument can improve the visibility of the markers to an overhead tracking system. Likewise, the angle can be selected by varying the difference between the heights of the first and second standoffs based on the intended use of the instrument to help maintain the constellation directly facing (e.g., parallel to) the tracking system during an intended procedure using the instrument. Further, by mounting the support orthogonal to the instrument and angling the markers by varying the heights of the first and second standoffs, the likelihood of significant tracking error caused by tolerances in the manufacturing process can be reduced compared to mounting the support at an angle relative to the instrument.

Specific details of several embodiments of the present technology are described herein with reference to FIGS. 1-4E. The present technology, however, can be practiced without some of these specific details. In some instances, well-known structures and techniques often associated with camera arrays, light field cameras, image reconstruction, registration processes, user interfaces, optical tracking, object tracking, marker balls, and the like have not been shown in detail so as not to obscure the present technology. Moreover, although frequently described in the context of tracking surgical instruments relative to a surgical scene (e.g., a spinal surgical scene), the methods and systems of the present technology can be used to track other types of objects relative to other scenes.

The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying figures depict embodiments of the present technology and are not intended to be limiting of its scope. Depicted elements are not necessarily drawn to scale, and various elements can be arbitrarily enlarged to improve legibility. Component details can be abstracted in the figures to exclude details as such details are unnecessary for a complete understanding of how to make and use the present technology. Many of the details, dimensions, angles, and other features shown in the Figures are merely illustrative of particular embodiments of the disclosure. Accordingly, other embodiments can have other dimensions, angles, and features without departing from the spirit or scope of the present technology.

The headings provided herein are for convenience only and should not be construed as limiting the subject matter disclosed.

I. SELECTED EMBODIMENTS OF IMAGING SYSTEMS

FIG. 1 is a schematic view of an imaging system 100 ("system 100") in accordance with embodiments of the present technology. In some embodiments, the system 100 can be a synthetic augmented reality system, a virtual-reality imaging system, an augmented-reality imaging system, a mediated-reality imaging system, and/or a non-immersive computational imaging system. In the illustrated embodiment, the system 100 includes a processing device 102 that is communicatively coupled to one or more display devices 104, one or more input controllers 106, and a camera array 110. In other embodiments, the system 100 can comprise additional, fewer, or different components. In some embodiments, the system 100 can include some features that are generally similar or identical to those of the mediated-reality imaging systems disclosed in (i) U.S. patent application Ser. No. 16/586,375, titled "CAMERA ARRAY FOR A MEDIATED-REALITY SYSTEM," and filed Sep. 27, 2019 and/or (ii) U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," and filed May 12, 2020, each of which is incorporated herein by reference in its entirety.

In the illustrated embodiment, the camera array 110 includes a plurality of cameras 112 (identified individually as cameras 112a-112n; which can also be referred to as first cameras) that are each configured to capture images of a scene 108 from a different perspective (e.g., first image data). The scene 108 might include for example, a patient undergoing surgery or another medical procedure. In other embodiments, the scene 108 can be another type of scene. The camera array 110 further includes a plurality of dedicated object tracking hardware 113 (identified individually as trackers 113a-113n) configured to capture positional data of one more objects, such as an instrument 101 (e.g., a surgical instrument or tool) having a tip 109, to track the movement and/or orientation of the objects through/in the scene 108. In some embodiments, the cameras 112 and the trackers 113 are positioned at fixed locations and orientations (e.g., poses) relative to one another. For example, the cameras 112 and the trackers 113 can be structurally secured by/to a mounting structure (e.g., a frame) at predefined fixed locations and orientations. In some embodiments, the cameras 112 can be positioned such that neighboring cameras 112 share overlapping views of the scene 108. In general, the position of the cameras 112 can be selected to maximize clear and accurate capture of all or a selected portion of the scene 108. Likewise, the trackers 113 can be positioned such that neighboring trackers 113 share overlapping views of the scene 108. Therefore, all or a subset of the cameras 112 and the trackers 113 can have different extrinsic parameters, such as position and orientation.

In some embodiments, the cameras 112 in the camera array 110 are synchronized to capture images of the scene 108 simultaneously (within a threshold temporal error). In some embodiments, all or a subset of the cameras 112 can be light field/plenoptic/RGB cameras that are configured to capture information about the light field emanating from the scene 108 (e.g., information about the intensity of light rays in the scene 108 and also information about a direction the light rays are traveling through space). Therefore, in some embodiments the images captured by the cameras 112 can encode depth information representing a surface geometry of the scene 108. In some embodiments, the cameras 112 are substantially identical. In other embodiments, the cameras 112 can include multiple cameras of different types. For example, different subsets of the cameras 112 can have different intrinsic parameters such as focal length, sensor type, optical components, and the like. The cameras 112 can have charge-coupled device (CCD) and/or complementary metal-oxide semiconductor (CMOS) image sensors and associated optics. Such optics can include a variety of configurations including lensed or bare individual image sensors in combination with larger macro lenses, micro-lens arrays, prisms, and/or negative lenses. For example, the cameras 112 can be separate light field cameras each having their own image sensors and optics. In other embodiments, some or all of the cameras 112 can comprise separate microlenslets (e.g., lenslets, lenses, microlenses) of a micro-lens array (MLA) that share a common image sensor.

In some embodiments, the trackers 113 are imaging devices, such as infrared (IR) cameras that are each configured to capture images of the scene 108 from a different perspective compared to other ones of the trackers 113. Accordingly, the trackers 113 and the cameras 112 can have different spectral sensitives (e.g., infrared vs. visible wavelength). In some embodiments, the trackers 113 are configured to capture image data of a plurality of optical markers (e.g., fiducial markers, marker balls) in the scene 108, such as markers 111 coupled to the instrument 101. In the illustrated embodiment, the markers 111 are attached to a common tracking support or constellation 130 and secured to the instrument 101 via the constellation 130. As described in greater detail below with reference to FIGS. 3A-4E, the constellation 130 can extend orthogonal to an axis of the instrument 101, and the markers 111 can be vertically offset relative to the constellation 130. In some aspects of the present technology, this arrangement can reduce error in tracking the instrument 101, and specifically error in tracking a position of the tip 109 of the instrument 101.

In the illustrated embodiment, the camera array 110 further includes a depth sensor 114. In some embodiments, the depth sensor 114 includes (i) one or more projectors 116 configured to project a structured light pattern onto/into the scene 108 and (ii) one or more depth cameras 118 (which can also be referred to as second cameras) configured to capture second image data of the scene 108 including the structured light projected onto the scene 108 by the projector 116. The projector 116 and the depth cameras 118 can operate in the same wavelength and, in some embodiments, can operate in a wavelength different than the cameras 112. For example, the cameras 112 can capture the first image data in the visible spectrum, while the depth cameras 118 capture the second image data in the infrared spectrum. In some embodiments, the depth cameras 118 have a resolution that is less than a resolution of the cameras 112. For example, the depth cameras 118 can have a resolution that is less than 70%, 60%, 50%, 40%, 30%, or 20% of the resolution of the cameras 112. In other embodiments, the depth sensor 114 can include other types of dedicated depth detection hardware (e.g., a LiDAR detector) for determining the surface geometry of the scene 108. In other embodiments, the camera array 110 can omit the projector 116 and/or the depth cameras 118.

In the illustrated embodiment, the processing device 102 includes an image processing device 103 (e.g., an image processor, an image processing module, an image processing unit), a registration processing device 105 (e.g., a registration processor, a registration processing module, a registration processing unit), and a tracking processing device 107 (e.g., a tracking processor, a tracking processing module, a tracking processing unit). The image processing device 103 is configured to (i) receive the first image data captured by the cameras 112 (e.g., light field images, light field image data, RGB images) and depth information from the depth sensor 114 (e.g., the second image data captured by the depth cameras 118), and (ii) process the image data and depth information to synthesize (e.g., generate, reconstruct, render) a three-dimensional (3D) output image of the scene 108 corresponding to a virtual camera perspective. The output image can correspond to an approximation of an image of the scene 108 that would be captured by a camera placed at an arbitrary position and orientation corresponding to the virtual camera perspective. In some embodiments, the image processing device 103 is further configured to receive and/or store calibration data for the cameras 112 and/or the depth cameras 118 and to synthesize the output image based on the image data, the depth information, and/or the calibration data. More specifically, the depth information and calibration data can be used/combined with the images from the cameras 112 to synthesize the output image as a 3D (or stereoscopic 2D) rendering of the scene 108 as viewed from the virtual camera perspective. In some embodiments, the image processing device 103 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," and filed Jun. 28, 2019, which is incorporated herein by reference in its entirety. In other embodiments, the image processing device 103 is configured to generate the virtual camera perspective based only on the images captured by the cameras 112—without utilizing depth information from the depth sensor 114. For example, the image processing device 103 can generate the virtual camera perspective by interpolating between the different images captured by one or more of the cameras 112.

The image processing device 103 can synthesize the output image from images captured by a subset (e.g., two or more) of the cameras 112 in the camera array 110, and does not necessarily utilize images from all of the cameras 112. For example, for a given virtual camera perspective, the processing device 102 can select a stereoscopic pair of images from two of the cameras 112 that are positioned and oriented to most closely match the virtual camera perspective. In some embodiments, the image processing device 103 (and/or the depth sensor 114) is configured to estimate a depth for each surface point of the scene 108 relative to a common origin and to generate a point cloud and/or a 3D mesh that represents the surface geometry of the scene 108. For example, in some embodiments the depth cameras 118 of the depth sensor 114 can detect the structured light projected onto the scene 108 by the projector 116 to estimate depth information of the scene 108. In some embodiments, the image processing device 103 can estimate depth from multiview image data from the cameras 112 using techniques such as light field correspondence, stereo block matching, photometric symmetry, correspondence, defocus, block matching, texture-assisted block matching, structured light, and the like, with or without utilizing information collected by the depth sensor 114. In other embodiments, depth may be acquired by a specialized set of the cameras 112 performing the aforementioned methods in another wavelength.

In some embodiments, the registration processing device 105 is configured to receive and/or store previously-captured image data, such as image data of a three-dimensional volume of a patient (3D image data). The image data can include, for example, computerized tomography (CT) scan data, magnetic resonance imaging (MM) scan data, ultrasound images, fluoroscope images, and/or other medical or other image data. The registration processing device 105 is further configured to register the preoperative image data to the real-time images captured by the cameras 112 and/or the depth sensor 114 by, for example, determining one or more transforms/transformations/mappings between the two. The processing device 102 (e.g., the image processing device 103) can then apply the one or more transforms to the preoperative image data such that the preoperative image data can be aligned with (e.g., overlaid on) the output image of the scene 108 in real-time or near real time on a frame-by-frame basis, even as the virtual perspective changes. That is, the image processing device 103 can fuse the preoperative image data with the real-time output image of the scene 108 to present a mediated-reality view that enables, for example, a surgeon to simultaneously view a surgical site in the scene 108 and the underlying 3D anatomy of a patient undergoing an operation. In some embodiments, the registration processing device 105 can register the previously-captured image data to the real-time images by using any of the methods disclosed in U.S. patent application Ser. No. 17/140,885, titled "METHODS AND SYSTEMS FOR REGISTERING PREOPERATIVE IMAGE DATA TO INTRAOPERATIVE IMAGE DATA OF A SCENE, SUCH AS A SURGICAL SCENE," and filed Jan. 4, 2021, which is incorporated herein by reference in its entirety.

In some embodiments, the tracking processing device 107 can process positional data captured by the trackers 113 to track objects (e.g., the instrument 101) within the vicinity of the scene 108. For example, the tracking processing device 107 can determine the position of the markers 111 in the 2D images captured by two or more of the trackers 113, and can compute the 3D position of the markers 111 via triangulation of the 2D positional data. More specifically, in some embodiments the trackers 113 include dedicated processing hardware for determining positional data from captured images, such as a centroid of the markers 111 in the captured images. The trackers 113 can then transmit the positional data to the tracking processing device 107 for determining the 3D position of the markers 111. In other embodiments, the tracking processing device 107 can receive the raw image data from the trackers 113. In a surgical application, for example, the tracked object may comprise a surgical instrument, an implant, a hand or arm of a physician or assistant, and/or another object having the markers 111 mounted thereto. In some embodiments, the processing device 102 can recognize the tracked object as being separate from the scene 108, and can apply a visual effect to the 3D output image to distinguish the tracked object by, for example, highlighting the object, labeling the object, and/or applying a transparency to the object.

In some embodiments, functions attributed to the processing device 102, the image processing device 103, the registration processing device 105, and/or the tracking processing device 107 can be practically implemented by two or more physical devices. For example, in some embodiments a synchronization controller (not shown) controls images displayed by the projector 116 and sends synchronization signals to the cameras 112 to ensure synchronization between the cameras 112 and the projector 116 to enable fast, multi-frame, multi-camera structured light scans. Additionally, such a synchronization controller can operate as a parameter server that stores hardware specific configurations such as parameters of the structured light scan, camera settings, and camera calibration data specific to the camera configuration of the camera array 110. The synchronization controller can be implemented in a separate physical device from a display controller that controls the display device 104, or the devices can be integrated together.

The processing device 102 can comprise a processor and a non-transitory computer-readable storage medium that stores instructions that when executed by the processor, carry out the functions attributed to the processing device 102 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the present technology described below can be stored or distributed on computer-readable media, including magnetic and optically readable and removable computer discs, stored as in chips (e.g., EEPROM or flash memory chips). Alternatively, aspects of the present technology can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the present technology.

The virtual camera perspective is controlled by an input controller 106 that update the virtual camera perspective based on user driven changes to the camera's position and rotation. The output images corresponding to the virtual camera perspective can be outputted to the display device 104. In some embodiments, the image processing device 103 can vary the perspective, the depth of field (e.g., aperture), the focus plane, and/or another parameter of the virtual camera (e.g., based on an input from the input controller) to generate different 3D output images without physically moving the camera array 110. The display device 104 is configured to receive output images (e.g., the synthesized 3D rendering of the scene 108) and to display the output images for viewing by one or more viewers. In some embodiments, the processing device 102 can receive and process inputs from the input controller 106 and process the captured images from the camera array 110 to generate output images corresponding to the virtual perspective in substantially real-time as perceived by a viewer of the display device 104 (e.g., at least as fast as the frame rate of the camera array 110).

Additionally, the display device 104 can display a graphical representation on/in the image of the virtual perspective of any (i) tracked objects within the scene 108 (e.g., a surgical tool) and/or (ii) registered or unregistered preoperative image data. That is, for example, the system 100 (e.g., via the display device 104) can blend augmented data into the scene 108 by overlaying and aligning information on top of "passthrough" images of the scene 108 captured by the cameras 112. Moreover, the system 100 can create a mediated reality experience where the scene 108 is reconstructed using light field image date of the scene 108 captured by the cameras 112, and where instruments are virtually represented in the reconstructed scene via information from the trackers 113. Additionally or alternatively, the system 100 can remove the original scene 108 and completely replace it with a registered and representative arrangement of the preoperatively captured image data, thereby removing information in the scene 108 that is not pertinent to a user's task.

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. The virtual camera perspective can then be derived to correspond to the position and orientation of the head-mounted display device 104 in the same reference frame and at the calculated depth (e.g., as calculated by the depth sensor 114) such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller, etc.) that enables a viewer to manually control the virtual perspective displayed by the display device 104.

Figure 2:
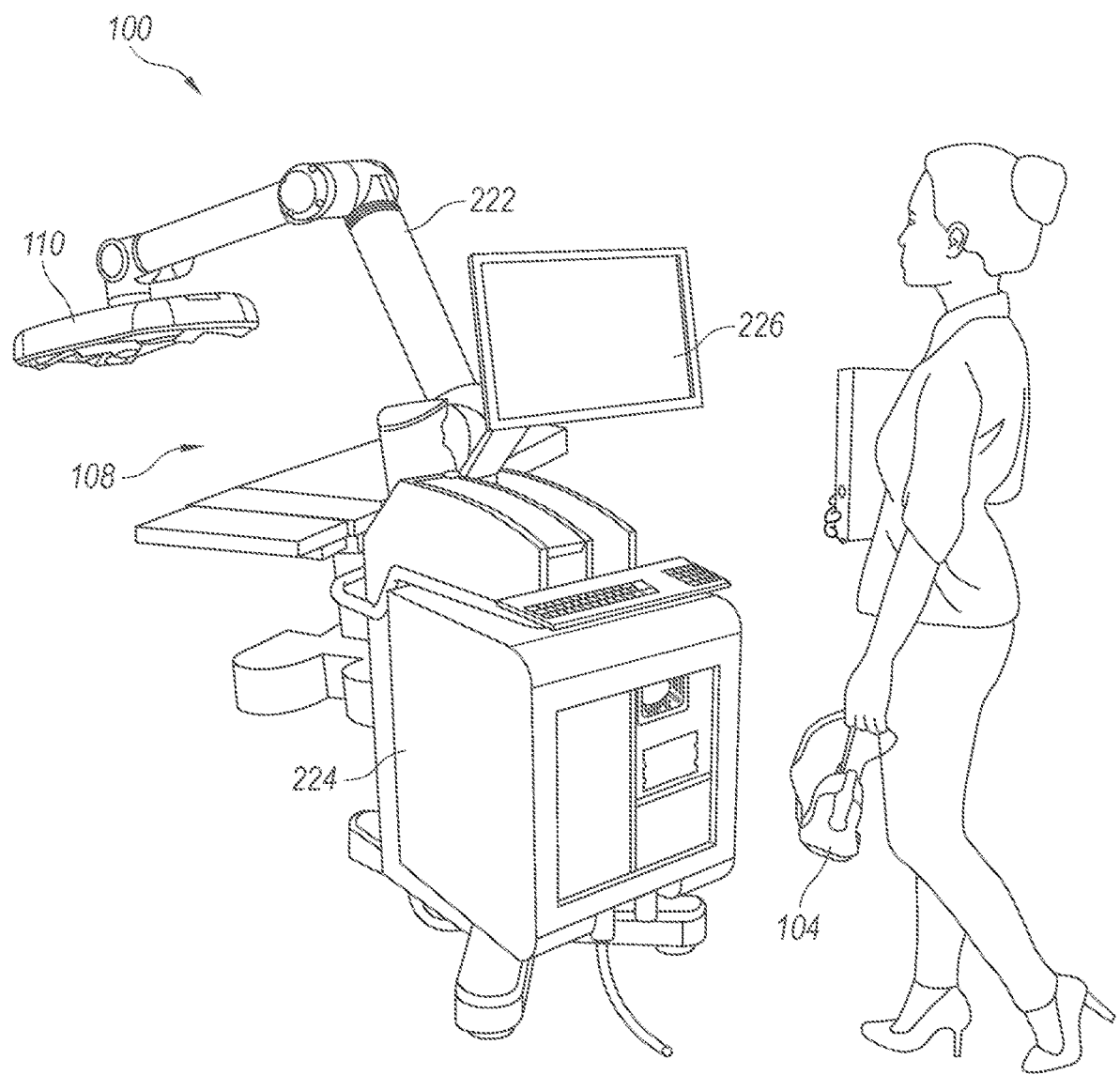
FIG. 2 is a perspective view of a surgical environment employing the imaging system of FIG. 1 for a surgical application in accordance with embodiments of the present technology.

FIG. 2 is a perspective view of a surgical environment employing the system 100 for a surgical application in accordance with embodiments of the present technology. In the illustrated embodiment, the camera array 110 is positioned over the scene 108 (e.g., a surgical site) and supported/positioned via a movable arm 222 that is operably coupled to a workstation 224. In some embodiments, the arm 222 can be manually moved to position the camera array 110 while, in other embodiments, the arm 222 can be robotically controlled in response to the input controller 106 (FIG. 1) and/or another controller. In the illustrated embodiment, the display device 104 is a head-mounted display device (e.g., a virtual reality headset, augmented reality headset, etc.). The workstation 224 can include a computer to control various functions of the processing device 102, the display device 104, the input controller 106, the camera array 110, and/or other components of the system 100 shown in FIG. 1. Accordingly, in some embodiments the processing device 102 and the input controller 106 are each integrated in the workstation 224. In some embodiments, the workstation 224 includes a secondary display 226 that can display a user interface for performing various configuration functions, a mirrored image of the display on the display device 104, and/or other useful visual images/indications. In other embodiments, the system 100 can include more or fewer display devices. For example, in addition to the display device 104 and the secondary display 226, the system 100 can include another display (e.g., a medical grade computer monitor) visible to the user wearing the display device 104.

II. SELECTED EMBODIMENTS OF CONSTELLATIONS FOR TRACKING TOOLS

Figure 3A:
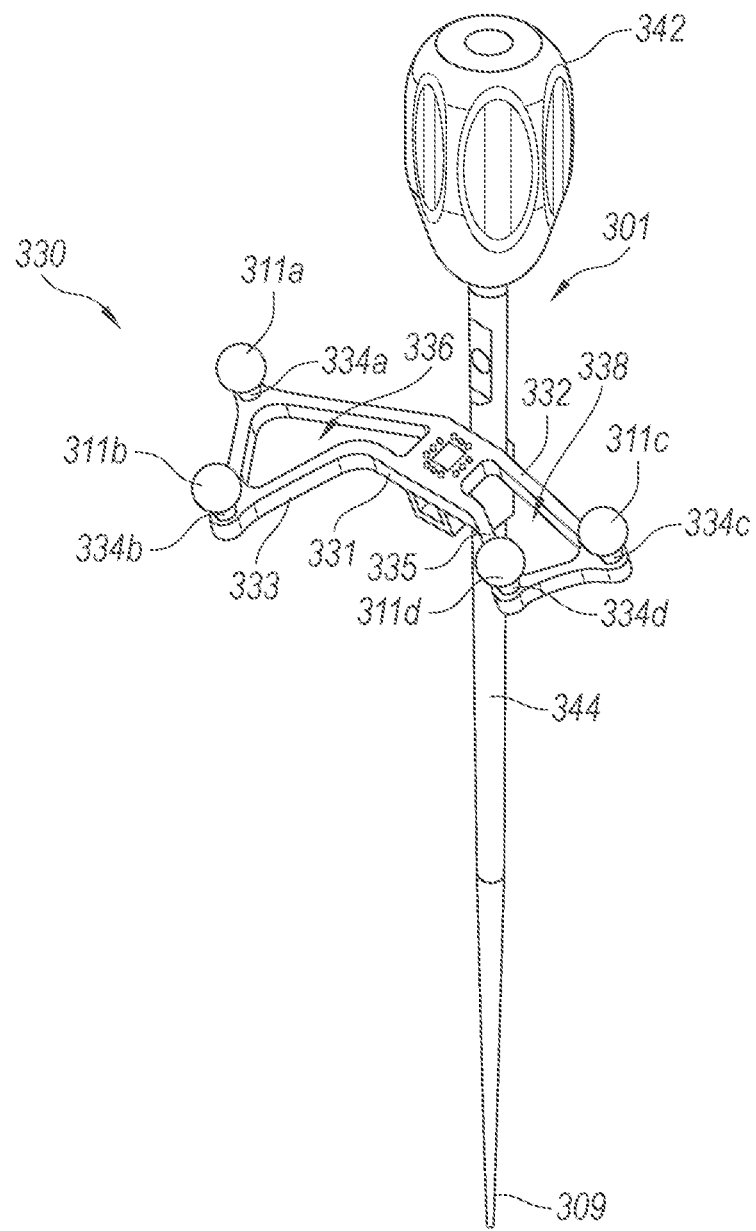
FIGS. 3A and 3B are an isometric view and a side view, respectively, of a tracking constellation attached to an instrument in accordance with embodiments of the present technology.
Figure 3B:
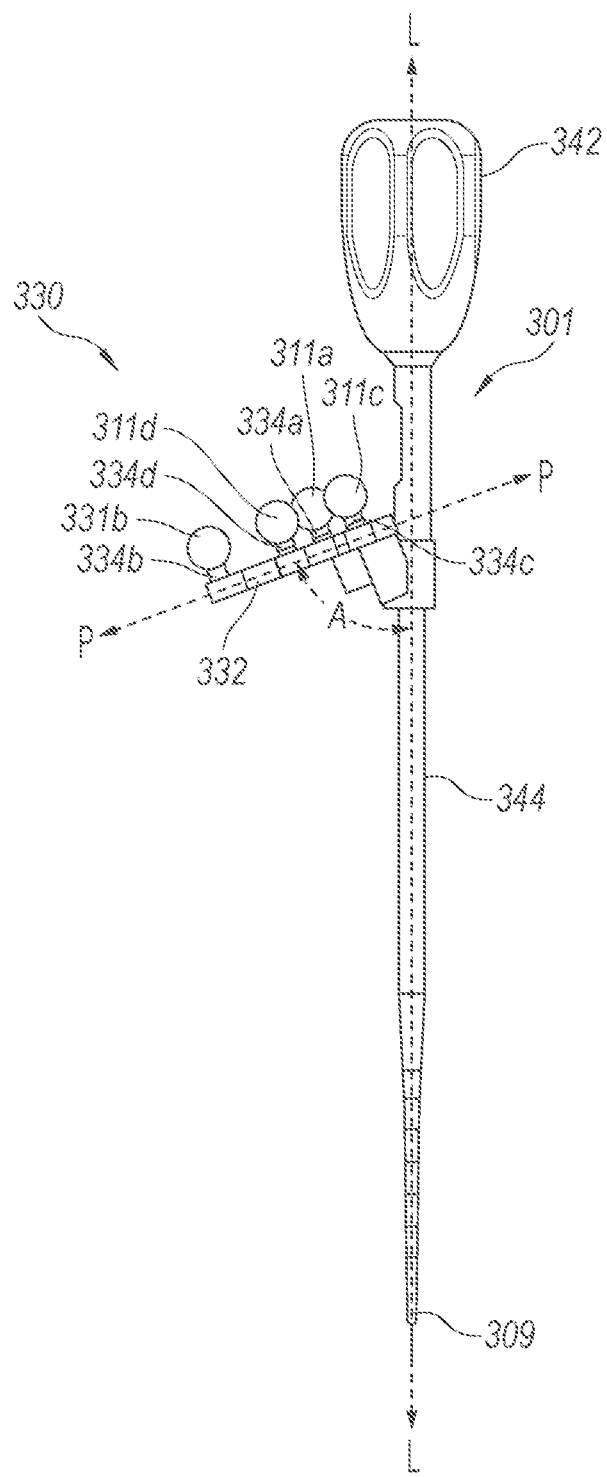
Figure 3C:
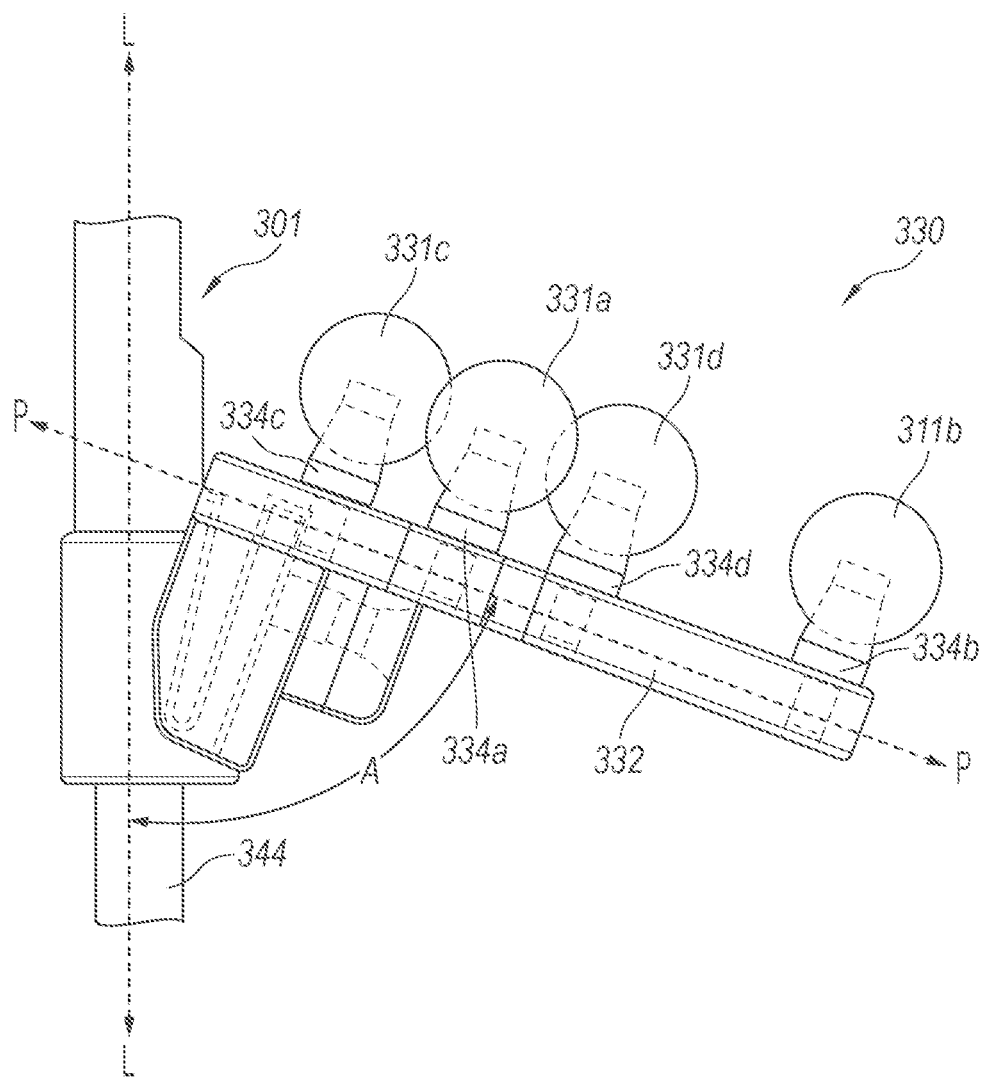
FIG. 3C is an enlarged side view of the tracking constellation of FIGS. 3A and 3B attached to the instrument in accordance with embodiments of the present technology.

FIGS. 3A and 3B are an isometric view and a side view, respectively, of a tracking constellation 330 attached to a tool or instrument 301 in accordance with embodiments of the present technology. FIG. 3C is an enlarged side view of the constellation 330 attached to the instrument 301 in accordance with embodiments of the present technology. Referring to FIGS. 3A-3C together, the instrument 301 can be a surgical tap, surgical probe, or other type of surgical or non-surgical instrument. In the illustrated embodiment, the instrument 301 includes a handle 342 releasably or permanently coupled to an elongate shaft 344 having a tip 309. The elongate shaft 344 can extend along a longitudinal axis L (FIGS. 3B and 3C). In other embodiments, the instrument 301 can be another type of instrument and/or can have different sizes, dimensions, shapes, and/or components.

In the illustrated embodiment, the constellation 330 includes a rigid support 332 (e.g., a frame, a support member) carrying a plurality of markers 311 (identified individually as first through fourth markers 311a-d, respectively). The markers 311 are shown as partially transparent in FIG. 3C for clarity. In some embodiments, the markers 311 are marker balls configured to reflect infrared light emitted and/or visible by the trackers 113 (FIG. 1). In other embodiments, the markers 311 can have other shapes and/or properties for tracking via different tracking systems. The support 332 can be integrally formed with the shaft 344 of the instrument 301 or rigidly coupled to the shaft 344 via a press fit, one or more fasteners (e.g., screws), adhesives, welding, and/or other suitable connections. The support 332 can be formed of suitably strong and rigid materials, such as metal (e.g., stainless steel, aluminum), plastic, and the like.

In the illustrated embodiment, the support 332 has a general planar shape that lays in a plane coincident with an axis P (FIGS. 3B and 3C). The plane coincident with the axis P can extend at an angle A (FIGS. 3B and 3C) of between about 5°-50°, between about 10°-30°, between about 15°-25°, about 20°, and the like relative to the longitudinal axis L of the instrument 301. The markers 311 can each be mounted to the support 332 via a corresponding one of a plurality of posts 334 (e.g., standoffs; identified individually as first through fourth posts 334a-d, respectively). As best seen in FIG. 3C, the markers 311 can be press fit onto the posts 334 while, in other embodiments, the markers 311 can be secured to the posts 334 via fasteners, adhesives, or other suitable couplings. In the illustrated embodiment, each of the posts 334 has generally the same height such that the markers 311 lay in a plane extending generally parallel to the support 332 (and the plane coincident with the axis P)—and therefore at the angle A relative to the longitudinal axis L.

Referring to FIG. 3A, in the illustrated embodiment the support 332 has (i) a central portion 331 coupled to the instrument 301, (ii) a first side portion 333 extending from the central portion 331, and (iii) a second side portion 335 extending from the central portion 331 opposite the first side portion 333. In the illustrated embodiment, the first and second markers 311a-b are mounted to the first and second posts 334a-b, respectively, along an outer periphery of the first side portion 333 in respective corners of the first side portion 333. Likewise, the third and fourth markers 311c-d are mounted to the third and fourth posts 334c-d, respectively, along an outer periphery of the second side portion 335 in respective corners of the second side portion 335. In other embodiments, the constellation 330 can include more or fewer of the markers 311 (e.g., more than four of the markers 311) and/or the markers 311 can be mounted differently about the support 332.

The first and second side portions 333, 335 can have different (e.g., unique) shapes and/or dimensions such that the markers 311 are each mounted at a different location and distance relative to the instrument 301. For example, in the illustrated embodiment, the first side portion 333 is larger (e.g., wider and longer) than the second side portion 335 such that the first and second markers 311a-b are positioned farther from the shaft 344 of the instrument 301 and from one another than the third and fourth markers 311c-d are mounted from the shaft 344 and one another. In some aspects of the present technology, this arrangement can allow the system 100 (FIG. 1) to uniquely determine a position, directionality, and/or orientation of the instrument 301, as described in greater detail below. In other embodiments, the first and second side portions 333, 335 can have the same shape and dimensions, and/or the support 332 can include more or fewer than the two illustrated side portions 333, 335. Moreover, in the illustrated embodiment the first and second side portions 333, 335 are each angled away from the central portion 331 and the shaft 344 such that, for example, the markers 311 are not below and obscured by the handle 342. In some embodiments, the first side portion 333 defines/includes a first opening 336 and the second side portion 335 defines/includes a second opening 338. The first and second openings 336, 338 can reduce the weight and/or manufacturing cost of the support 332. In other embodiments, the support 332 can define/include more or fewer than the two illustrated openings 336, 338.

Referring to FIGS. 1-3C together, the system 100 can determine the position of the instrument 301 by tracking (e.g., imaging) the markers 311 with the trackers 113 of the camera array 110. More specifically, the position and orientation of the constellation 330 relative to the instrument 301 (e.g., the tip 309) can be determined/defined via a calibration (e.g., measurement) process and/or during engineering or production of the constellation 330 and instrument 301. That is, the position and orientation of the constellation 330 and the instrument 301 can be defined in the same coordinate reference frame. Accordingly, during use of the system 100, the position and orientation of the instrument 301 can be determined based on the position and orientation of the constellation 330 as determined by the trackers 113.

Notably, however, the system 100 can only accurately track the instrument 301 if some or all of the markers 311 are visible to the trackers 113. In some aspects of the present technology, mounting the support 332 and the coupled markers 311 at the angle A relative to the instrument 301 can improve the visibility of the markers 311 to the trackers 113 in the overhead camera array 110. More specifically, because the camera array 110 is configured to be positioned generally overhead above the scene 108, positioning the markers 311 at an angle relative to the instrument 301 can help ensure that the markers 311 are visible to the trackers 113 during substantially an entire procedure using the instrument 301.

In contrast, some conventional instrument tracking systems position trackers away from the scene such that the markers must be mounted in a plane generally parallel to the instrument to remain visible to the trackers. Moreover, the angle A can be selected to generally correspond to an angle at which a user will hold the tool during an operation such that more of the markers 311 face the overhead trackers 113 during the procedure—thereby increasing the visibility of the markers 311 to the trackers 113 during the procedure. That is, the angle A can be selected based on the intended use of the instrument 301 to help maintain the constellation 330 directly facing (e.g., parallel to) the camera array 110 and the mounted trackers 113 during an intended procedure, thereby reducing the likelihood that one or more of the markers 311 becomes occluded during the procedure.

Figure 4A:
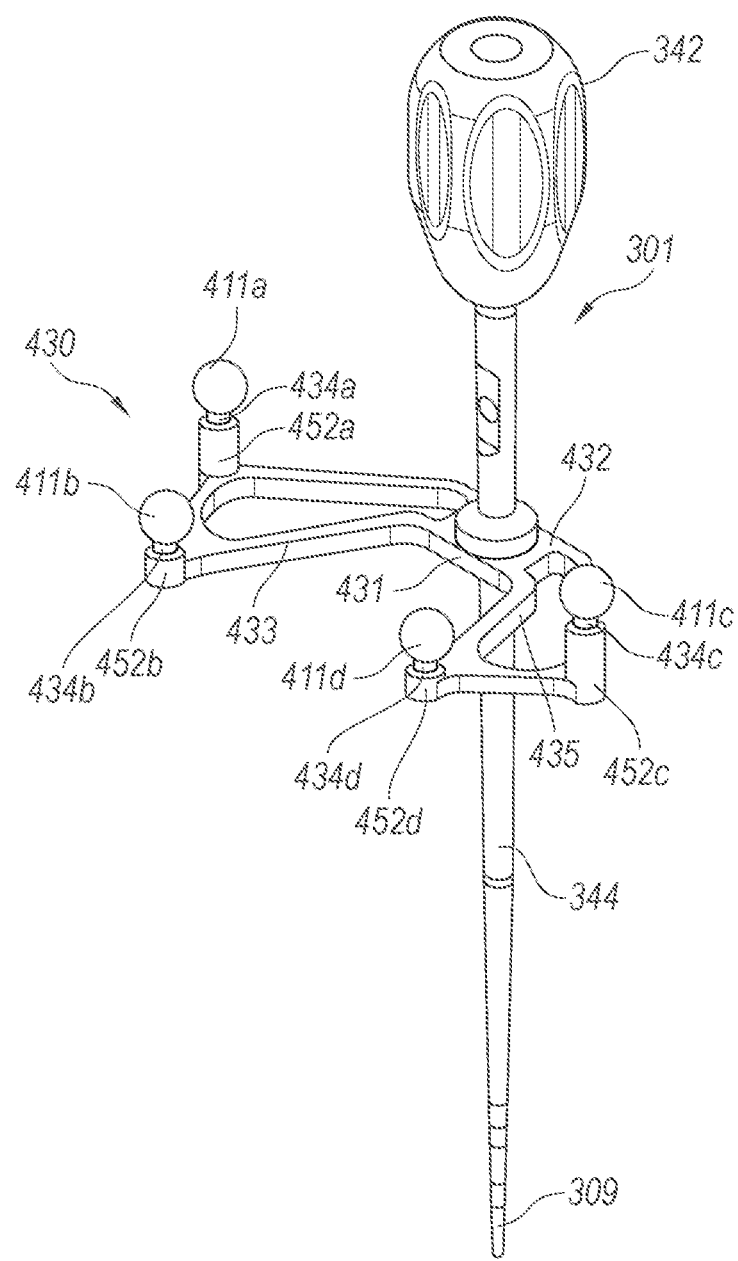
FIGS. 4A-4C are an isometric view, a side view, and an exploded view, respectively, of a tracking constellation attached to the instrument in accordance with additional embodiments of the present technology.
Figure 4B:
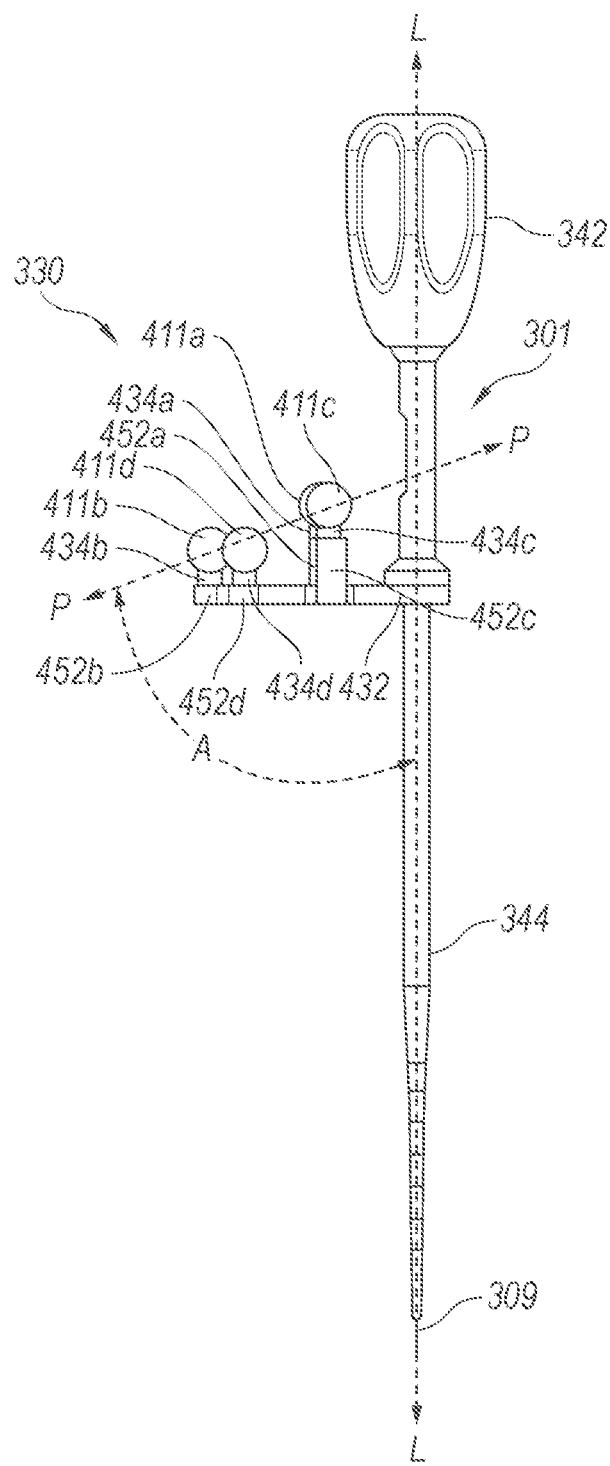
Figure 4C:
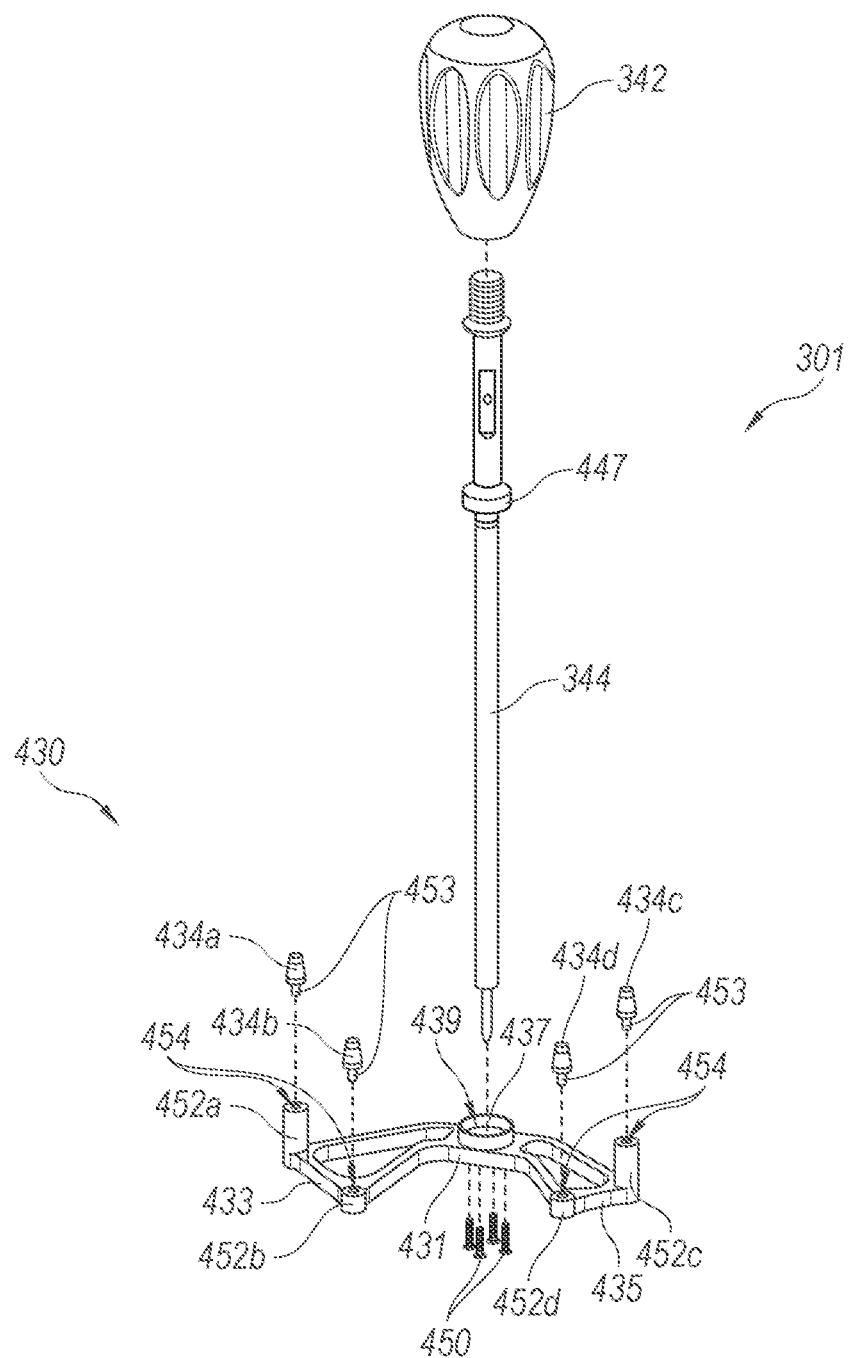
Figure 4D:
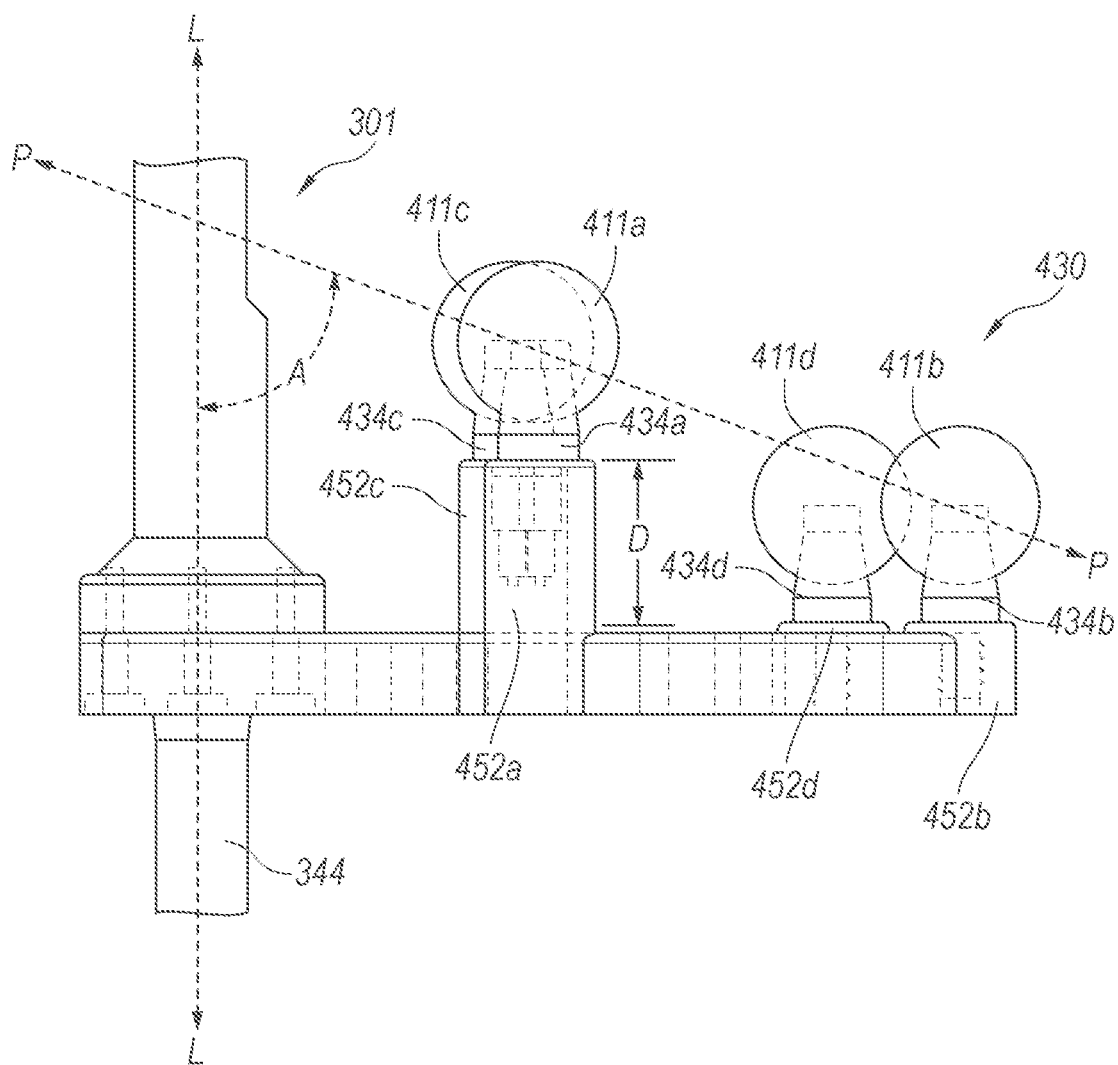
FIG. 4D is an enlarged side view of the tracking constellation of FIGS. 4A-4C attached to the instrument in accordance with embodiments of the present technology.

FIGS. 4A-4C are an isometric view, a side view, and an exploded view, respectively, of a tracking constellation 430 attached to the instrument 301 in accordance with additional embodiments of the present technology. FIG. 4D is an enlarged side view of the constellation 430 attached to the instrument 301 in accordance with embodiments of the present technology. Referring to FIGS. 4A-4D together, the constellation 430 can include some features that are at least generally similar in structure and function, or identical in structure and function, to the corresponding features of the constellation 330 described in detail above with reference to FIGS. 3A-4C, and can operate in a generally similar or identical manner to the constellation 330.

In the illustrated embodiment, for example, the constellation 430 includes a rigid support 432 carrying a plurality of markers 411 (identified individually as first through fourth markers 411a-d, respectively) mounted to a corresponding one of a plurality of posts 434 (identified individually as first through fourth posts 434a-d, respectively). The markers 411 are omitted in FIG. 4C and shown as partially transparent in FIG. 4D for clarity. Likewise, with reference to FIGS. 4A and 4C together, the support 432 includes (i) a central portion 431 coupled to the instrument 301, (ii) a first side portion 433 extending from the central portion 431, and (iii) a second side portion 435 extending from the central portion 431 opposite the first side portion 433. The first and second side portions 433, 435 can each have a different shape such that the markers 411 are uniquely positioned relative to the instrument 301. In other embodiments, the support 432 can include more or fewer than the two illustrated side portions 433, 435.

Figure 4E:
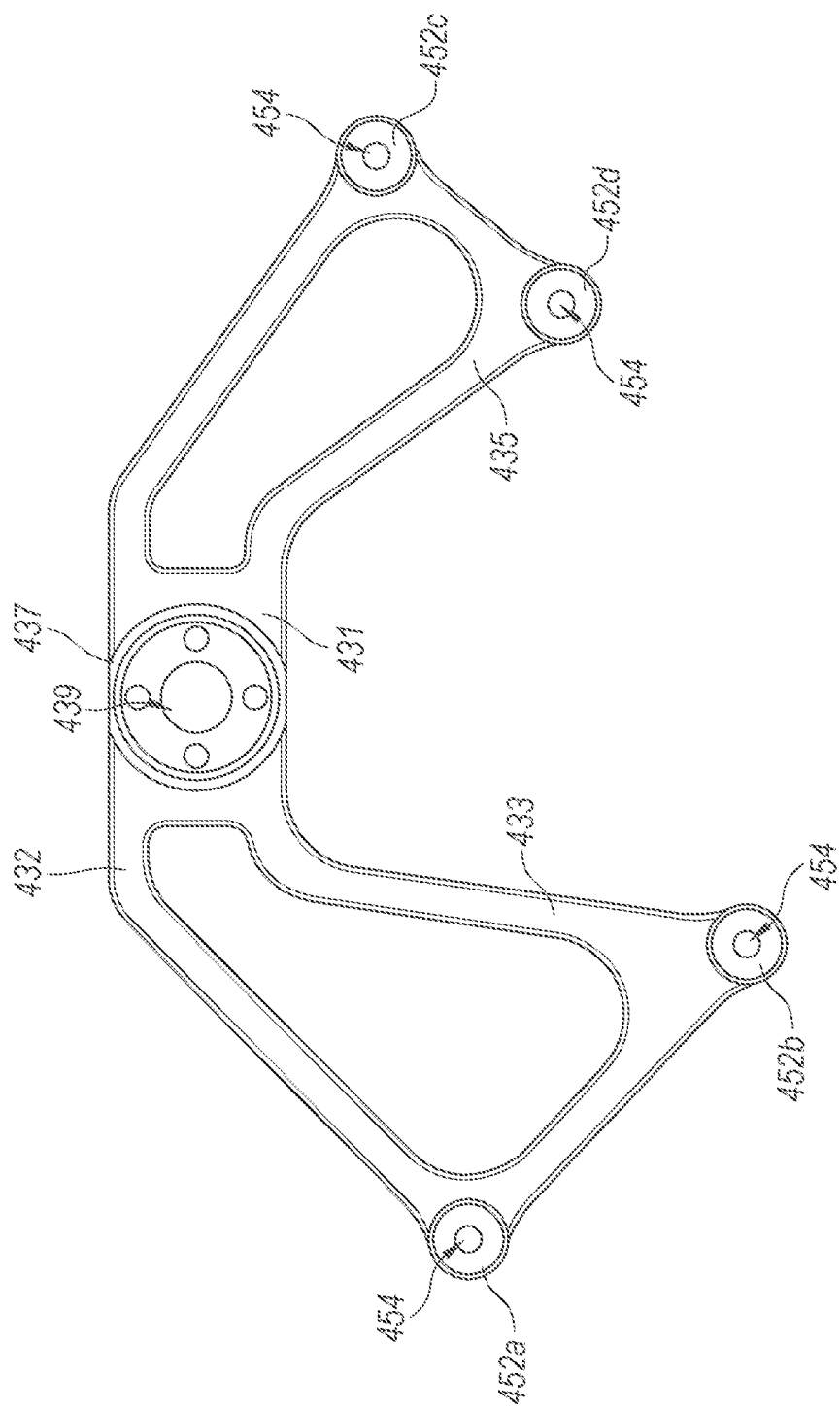
FIG. 4E is a top view of a support of the tracking constellation of FIGS. 4A-4C in accordance with embodiments of the present technology.

FIG. 4E is a top view of the support 432 in accordance with embodiments of the present technology. With reference to FIGS. 4C and 4E together, the central portion 431 of the support 432 includes a first coupling portion 437 and the instrument 301 includes a corresponding second coupling portion 447. The first and second coupling portions 437, 447 can be configured (e.g., shaped, sized) to engage one another to at least partially secure the constellation 430 to the instrument 301. In the illustrated embodiment, for example, the first coupling portion 437 has a ring shape configured to be positioned in a corresponding circular aperture formed between the shaft 344 of the instrument 301 and the second coupling portion 447. The central portion 431 can further include an aperture 439 extending therethrough in the first coupling portion 437. Accordingly, to install the constellation 430 on the instrument 301, the shaft 344 can be inserted into the aperture 439 and the constellation 430 can be slid along the shaft 344 until the first coupling portion 437 engages the second coupling portion 447. In some embodiments, the constellation 430 can be further secured to the instrument 301 via one or more fasteners 450, such as screws.

Referring to FIGS. 4A-4E together, the support 432 can extend generally orthogonal to the longitudinal axis L (FIGS. 4B and 4D) of the shaft 344 of the instrument 301. In the illustrated embodiment the constellation 430 further includes a plurality of standoffs 452 (identified individually as a first through fourth standoffs 452a-d, respectively) mounted to the support 432. In the illustrated embodiment, the standoffs 452 are integrally formed with the support 432 while, in other embodiments, the standoffs 452 can be separate components releasably or permanently coupled to the support 432. The standoffs 452 can extend generally orthogonal to the support 432 and therefore generally parallel to the longitudinal axis L. The first through fourth standoffs 452a-d receive the first through fourth posts 434a-d, respectively, and support the first through fourth markers 411a—d, respectively. More specifically, the posts 434 can be configured to be releasably or permanently coupled to the standoffs 452. For example, referring to FIG. 4C, in the illustrated embodiment the posts 434 each include a peg portion 453 configured (e.g., shaped, sized) to be press fit into a corresponding one of a plurality of holes 454 in the standoffs 452. In other embodiments, the posts 434 can be integrally formed with the support 432 and/or coupled to the standoffs 452 in other manners. While the posts 434 and the standoffs 452 are separate components in the illustrated embodiment, in other embodiments these components can be integrally formed or composed of additional intermediary components. Similarly, the posts 434 and standoffs 452 (and/or any intermediary components) can collectively be referred to as "posts," "standoffs," "columns," "supports," and/or the like. In other embodiments, the support 432 can include more or fewer than the four illustrated posts 434 and standoffs 452.

Referring again to FIGS. 4A-4E together, the first and second standoffs 452a-b extend from the first side portion 433 of the support 432 and the third and fourth standoffs 452c-d extends from the second side portion 435 of the support 432. In the illustrated embodiment, the first and third standoffs 452a, c (which can collectively be referred to as "first standoffs") extend to an elevation greater than the second and fourth standoffs 452b, d (which can collectively be referred to as "second standoffs"). More specifically, a difference D (FIG. 4D) between a height of the first and third standoffs 452a, c relative to a height of the second and fourth standoffs 452b, d can be between about 3-30 millimeters, between about 5-15 millimeters, between about 13-14 millimeters, about 13.7 millimeters, and the like. Accordingly, because the support 432 extends generally orthogonal to the longitudinal axis L, the standoffs 452 effectively support the markers 411 at different heights/positions along the longitudinal axis L to create an angle between the markers 411. In the illustrated embodiment, the first and third standoffs 452a, c have the same height and the second and fourth standoffs 452b, d have the same height such that the markers 411 are positioned along the plane coincident with the axis P (FIGS. 4B and 4D). In other embodiments, the standoffs 452 can have different heights to support the markers 411 at different positions.

Accordingly, similar to the constellation 330 described in detail above with reference to FIGS. 3A-3C, the constellation 430 can support the markers 411 along the plane coincident with the axis P at the angle A (FIGS. 4B and 4D). As described in detail above, mounting the markers 411 at the angle A relative to the instrument 301 can improve the visibility of the markers 411 to the trackers 113 in the overhead camera array 110 (FIGS. 1 and 2). Likewise, the angle A can be selected by varying the difference D between the heights of the standoffs 452 based on the intended use of the instrument 301 to help maintain the constellation 330 directly facing (e.g., parallel to) the camera array 110 and the mounted trackers 113 during an intended procedure, thereby reducing the likelihood that one or more of the markers 311 becomes occluded during the procedure. However, in contrast to the constellation 330, the support 432 need not be mounted at an oblique (e.g., non-orthogonal) angle relative to the shaft 344 of the instrument 301. In some aspects of the present technology, this arrangement can reduce tracking error compared to the constellation 330. In particular, manufacturing processes and/or machine tolerances for fabricating linear dimensions can typically be controlled at greater precession than angular dimensions. For example, linear dimensions can often be controlled to a precision of less than 0.1 millimeter while angular dimensions are often only controllable to a precision of ±0.5 millimeter. When the instrument 301 is long, even small changes in the angle of the constellation can cause relatively large errors in the tracked position of the tip 309 of the instrument. Accordingly, the constellation 430 can use only orthogonal angles (e.g., between the support 432 and the shaft 344 of the instrument 301 and between the support 432 and the standoffs 452) to angle the markers 411 relative to the shaft 344—reducing the likelihood of significant tracking error caused by tolerances in the manufacturing process.

III. ADDITIONAL EXAMPLES

The following examples are illustrative of several embodiments of the present technology:

1. A tracking constellation for use with an instrument, comprising:
a support;
a plurality of first standoffs extending from the support to a first height;
a plurality of second standoffs extending from the support to a second height different than the first height; and
a plurality of markers, wherein individual ones of the markers are mounted to a corresponding one of the first standoffs or the second standoffs, and wherein the markers lay in a common plane.
2. The tracking constellation of example 1 wherein the markers are marker balls configured to reflect infrared light.
3. The tracking constellation of example 1 or example 2 wherein the support is generally planar.
4. The tracking constellation of example 3 wherein the support is configured to extend generally orthogonal to a longitudinal axis of the instrument.
5. The tracking constellation of any one of examples 1–4 wherein the first and second standoffs extend generally orthogonal to the support.
6. The tracking constellation of any one of examples 1-5 wherein the support includes a central portion configured to be coupled to the instrument, a first side portion extending from the central portion, and a second side portion extending from the central portion, wherein the first and second side portions have different shapes.
7. The tracking constellation of example 6 wherein one of the first standoffs extends from the first side portion, wherein another one of the first standoffs extends from the second side portion, wherein one of the second standoffs extends from the first side portion, and wherein another one of the second standoffs extends from the second side portion.
8. The tracking constellation of any one of examples 1-7 wherein the support, the first standoffs, and the second standoffs are integrally formed.
9. A system, comprising:
an instrument having a longitudinal axis; and
a tracking constellation configured to be coupled to the instrument and including—
a support, wherein the support is generally planar, and wherein the support is configured to extend at a generally orthogonal angle to the longitudinal axis when the tracking constellation is coupled to the instrument;
a plurality of first standoffs extending from the support to a first height;
a plurality of second standoffs extending from the support to a second height different than the first height; and
a plurality of markers, wherein individual ones of the markers are mounted to a corresponding one of the first standoffs or the second standoffs.
10. The system of example 9 wherein the markers lay in a common plane.
11. The system of example 10 wherein the plane extends at an angle of between about 15°-25° relative to the longitudinal axis when the tracking constellation is coupled to the instrument.
12. The system of any one of examples 9-11 wherein each of the markers is positioned at a different distance from the longitudinal axis when the tracking constellation is coupled to the instrument.
13. The system of any one of examples 9-12 wherein the instrument is a surgical instrument.
14. The system of any one of examples 9-13 wherein the support includes a central portion configured to be coupled to the instrument, a first side portion extending from the central portion, and a second side portion extending from the central portion, wherein the first and second side portions have different shapes.
15. The system of any one of examples 9-14 wherein the instrument includes a shaft, wherein the support includes a central portion having an aperture, and wherein the shaft is configured to extend through the aperture when the tracking constellation is coupled to the instrument.
16. The tracking constellation of any one of examples 9-15 wherein the support, the first standoffs, and the second standoffs are integrally formed.
17. A system, comprising:
an instrument having a longitudinal axis;
a tracking constellation coupled to the instrument and including—
a support, wherein the support is generally planar, and wherein the support extends at a generally orthogonal angle to the longitudinal axis;
a plurality of first standoffs extending from the support to a first height;
a plurality of second standoffs extending from the support to a second height different than the first height; and
a plurality of markers, wherein individual ones of the markers are mounted to a corresponding one of the first standoffs or the second standoffs; and
a camera array including a plurality of trackers, wherein the camera array is positioned above the scene, and wherein the trackers are configured to capture image data of the markers within the scene.

18. The system of example 17, further comprising a processor communicatively coupled to the camera array and configured to process the image data to determine a position of the instrument within the scene.

19. The system of example 17 or example 18 wherein the markers lay in a common plane.

20. The system of any one of examples 17-19 wherein the plane extends at an angle of between about 15°-25° relative to the longitudinal axis.

IV. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A tracking constellation for use with an instrument comprising:
   a rigid support, wherein the support is planar and extends along a first plane, wherein the support includes an aperture positioned along a longitudinal axis, wherein the longitudinal axis is orthogonal to the first plane, and wherein the support is configured to receive the instrument in the aperture;
   a plurality of first standoffs extending from the support orthogonal to the first plane to a first height;
   a plurality of second standoffs extending from the support orthogonal to the first plane to a second height different than the first height; and
   a plurality of markers, wherein individual ones of the markers are mounted to a corresponding one of the first standoffs or the second standoffs, wherein the markers lay in a common second plane, and wherein the second plane extends at an acute angle to the first plane.

2. The tracking constellation of claim 1 wherein the markers are marker balls configured to reflect infrared light.

3. The tracking constellation of claim 1 wherein the support includes a central portion including the aperture, a first side portion extending from the central portion, and a second side portion extending from the central portion, wherein the first and second side portions have different shapes.

4. The tracking constellation of claim 3 wherein one of the first standoffs extends from the first side portion, wherein another one of the first standoffs extends from the second side portion, wherein one of the second standoffs extends from the first side portion, and wherein another one of the second standoffs extends from the second side portion.

5. The tracking constellation of claim 1 wherein the support, the first standoffs, and the second standoffs are integrally formed.

6. A system, comprising:
   an instrument having a longitudinal axis; and
   a tracking constellation configured to be coupled to the instrument and including—
      a rigid support, wherein the support includes an aperture configured to receive a portion of the instrument, wherein the support is planar, wherein the support extends along a first plane at an angle orthogonal to the longitudinal axis;
      a plurality of first standoffs extending from the support orthogonal to the first plane to a first height;
      a plurality of second standoffs extending from the support orthogonal to the first plane to a second height different than the first height; and
      a plurality of markers, wherein individual ones of the markers are mounted to a corresponding one of the first standoffs or the second standoffs.

7. The system of claim 6 wherein the markers lay in a common second plane, and wherein the second plane extends at an acute angle to the first plane.

8. The system of claim 7 wherein the acute angle is between 15°-25°.

9. The system of claim 6 wherein each of the markers is positioned at a different distance from the aperture.

10. The system of claim 6 wherein the instrument is a surgical instrument.

11. The system of claim 6 wherein the support includes a central portion including the aperture, a first side portion extending from the central portion, and a second side portion extending from the central portion, wherein the first and second side portions have different shapes such that each of the markers is a different distance from the aperture.

12. The system of claim 6 wherein the instrument includes a shaft, and wherein the shaft extends through the aperture when the aperture receives the portion of the instrument.

13. The system of claim 6 wherein the support, the first standoffs, and the second standoffs are integrally formed.

14. A system, comprising:
   an instrument having a longitudinal axis;
   a tracking constellation coupled to the instrument and including—
      a rigid support, wherein the support is planar, wherein the support extends along a first plane at an orthogonal angle to the longitudinal axis, and wherein the support includes an aperture configured to receive a portion of the instrument;

a plurality of first standoffs extending from the support orthogonal to the first plane to a first height;

a plurality of second standoffs extending from the support orthogonal to the first plane to a second height different than the first height; and a plurality of markers, wherein individual ones of the markers are mounted to a corresponding one of the first standoffs or the second standoffs; and a camera array including a plurality of trackers, wherein the camera array is positioned above a scene, and wherein the trackers are configured to capture image data of the markers within the scene.

15. The system of claim 14, further comprising a processor communicatively coupled to the camera array and configured to process the image data to determine a position of the instrument within the scene.

16. The system of claim 14 wherein the markers lay in a common second plane, and wherein the second plane extends at an acute angle to the first plane.

17. The system of claim 16 wherein the acute angle is between 15°-25°.

* * * * *

UNITED STATES PATENT AND TRADEMARK OFFICE
CERTIFICATE OF CORRECTION

PATENT NO. : 12,016,642 B2
APPLICATION NO. : 17/469599
DATED : June 25, 2024
INVENTOR(S) : Jason A. Schoen et al.

It is certified that error appears in the above-identified patent and that said Letters Patent is hereby corrected as shown below:

In the Specification

In Column 13, Line 54, delete "1~4" and insert -- 1-4 --.

In the Claims

In Column 15, Line 55, in Claim 1, delete "instrument" and insert -- instrument, --.

Signed and Sealed this
Thirteenth Day of August, 2024

Katherine Kelly Vidal
*Director of the United States Patent and Trademark Office*